United States Patent
Jansson et al.

(10) Patent No.: US 7,815,809 B2
(45) Date of Patent: Oct. 19, 2010

(54) METHOD FOR CONDUCTIVITY CALCULATION IN A TREATMENT FLUID UPSTREAM AND DOWNSTREAM A FILTRATION UNIT IN APPARATUSES FOR THE BLOOD TREATMENT

(75) Inventors: Olof Jansson, Vellinge (SE); Roland Persson, Limhamn (SE); Jan Peter Sternby, Lund (SE)

(73) Assignee: Gambro Lundia AB, Lund (SE)

( * ) Notice: Subject to any disclaimer, the term of this patent is extended or adjusted under 35 U.S.C. 154(b) by 1072 days.

(21) Appl. No.: 11/299,840

(22) Filed: Dec. 13, 2005

(65) Prior Publication Data

US 2007/0131595 A1    Jun. 14, 2007

(51) Int. Cl.
*C02F 1/00*    (2006.01)
(52) U.S. Cl. .................. 210/746; 210/96.2; 210/646; 210/650; 210/739; 422/82.02; 700/273; 137/5
(58) Field of Classification Search ............... 210/646, 210/650, 652, 746, 92.6, 739; 702/22, 30; 700/266, 273; 324/439; 604/5.01, 6.09, 604/65; 422/82.01, 82.02; 137/5
See application file for complete search history.

(56) References Cited

U.S. PATENT DOCUMENTS

| | | | | |
|---|---|---|---|---|
| 3,324,720 | A | * | 6/1967 | Sutherland ............... 73/861.07 |
| 4,136,563 | A | * | 1/1979 | Mueller et al. ........... 73/861.03 |
| 4,923,613 | A | * | 5/1990 | Chevallet .................... 210/647 |
| 5,024,756 | A | | 6/1991 | Sternby et al. |
| 5,100,554 | A | * | 3/1992 | Polaschegg ................ 210/647 |
| 5,230,702 | A | * | 7/1993 | Lindsay et al. ............. 604/4.01 |
| 5,243,539 | A | * | 9/1993 | Holt et al. ...................... 702/30 |
| 5,396,178 | A | * | 3/1995 | Rybarski ..................... 324/439 |
| 5,399,157 | A | * | 3/1995 | Goux et al. ................ 604/4.01 |
| 5,510,717 | A | * | 4/1996 | Buffaloe et al. ............. 324/445 |
| 5,567,320 | A | | 10/1996 | Goux et al. |
| 5,644,240 | A | * | 7/1997 | Brugger ...................... 324/439 |
| 5,662,806 | A | * | 9/1997 | Keshaviah et al. .......... 210/739 |
| 5,716,531 | A | * | 2/1998 | Kenley et al. ............... 210/746 |

(Continued)

FOREIGN PATENT DOCUMENTS

EP    0 547 025 A1    6/1993

(Continued)

*Primary Examiner*—Tony G Soohoo
*Assistant Examiner*—David C Mellon
(74) *Attorney, Agent, or Firm*—Finnegan, Henderson, Farabow, Garrett & Dunner, L.L.P.

(57) ABSTRACT

A method for conductivity calculation in a treatment fluid downstream a filtration unit in a blood treatment apparatus is provided. The conductivity calculation is then used for clearance and fistula flow determination. A flow of treatment fluid is created in the filtration unit; a change in the conductivity of the treatment fluid at the inlet of the filtration unit is imposed to cause an induced conductivity change in the fluid at the outlet of the filtration unit; a predetermined number of conductivity values Cdo downstream from the filtration unit are measured. The measured conductivity values define a curve the pattern of which is estimated by means of one interpolating mathematical function in an interval of time after the occurrence of the induced conductivity change; a characteristic measuring time $tcalc_{clr}$ is determined. The value of the interpolating mathematical function at the characteristic measuring time $tcalc_{clr}$ represents the conductivity value Cdo2 of the treatment fluid downstream from the filtration unit after the induced conductivity change.

78 Claims, 7 Drawing Sheets

U.S. PATENT DOCUMENTS

| | | | |
|---|---|---|---|
| 5,872,454 A * | 2/1999 | West | 324/439 |
| 5,928,180 A * | 7/1999 | Krivitski et al. | 604/6.09 |
| 5,938,938 A * | 8/1999 | Bosetto et al. | 210/739 |
| 5,954,951 A * | 9/1999 | Nuccio | 210/87 |
| 6,075,367 A * | 6/2000 | Brugger | 324/439 |
| 6,101,449 A * | 8/2000 | Givens et al. | 702/22 |
| 6,110,384 A * | 8/2000 | Goux et al. | 210/739 |
| 6,123,847 A * | 9/2000 | Bene | 210/646 |
| 6,139,754 A * | 10/2000 | Hartranft et al. | 210/739 |
| 6,187,199 B1 * | 2/2001 | Goldau | 210/646 |
| 6,217,539 B1 * | 4/2001 | Goldau | 604/4.01 |
| 6,258,027 B1 * | 7/2001 | Sternby | 600/366 |
| 6,269,313 B1 * | 7/2001 | Givens et al. | 702/22 |
| 6,452,371 B1 * | 9/2002 | Brugger | 324/71.1 |
| 6,614,212 B2 * | 9/2003 | Brugger et al. | 324/71.1 |
| 6,648,845 B1 * | 11/2003 | Gotch et al. | 604/5.01 |
| 6,683,464 B2 * | 1/2004 | Park et al. | 324/706 |
| 6,690,173 B2 * | 2/2004 | Blades | 324/439 |
| 6,691,040 B2 * | 2/2004 | Bosetto et al. | 702/19 |
| 6,702,774 B1 * | 3/2004 | Polaschegg | 604/5.01 |
| 6,767,333 B1 * | 7/2004 | Muller et al. | 604/6.09 |
| 6,860,866 B1 * | 3/2005 | Graf et al. | 604/5.01 |
| 6,861,266 B1 * | 3/2005 | Sternby | 436/178 |
| 6,966,979 B2 * | 11/2005 | Pedrazzi | 210/85 |
| 7,001,353 B2 * | 2/2006 | Bosetto et al. | 604/5.01 |
| 7,033,539 B2 * | 4/2006 | Krensky et al. | 422/44 |
| 7,067,061 B2 * | 6/2006 | Bosetto et al. | 210/647 |
| 7,077,819 B1 * | 7/2006 | Goldau et al. | 604/5.04 |
| 7,172,570 B2 * | 2/2007 | Cavalcanti et al. | 604/6.11 |
| 7,208,134 B2 * | 4/2007 | Bromberg et al. | 423/592.1 |
| 7,387,734 B2 * | 6/2008 | Felding | 210/646 |
| 7,435,235 B2 * | 10/2008 | Sternby | 604/6.09 |
| 7,473,371 B2 * | 1/2009 | Krivitski et al. | 210/739 |
| 7,488,447 B2 * | 2/2009 | Sternby | 422/44 |
| 7,749,184 B2 * | 7/2010 | Cavalcanti et al. | 604/6.11 |
| 2003/0164708 A1 * | 9/2003 | Park et al. | 324/439 |
| 2003/0217975 A1 * | 11/2003 | Yu et al. | 210/739 |
| 2003/0230533 A1 * | 12/2003 | Gross et al. | 210/646 |
| 2004/0060865 A1 * | 4/2004 | Callan et al. | 210/646 |
| 2004/0073153 A1 * | 4/2004 | Bosetto et al. | 604/5.03 |
| 2004/0186409 A1 * | 9/2004 | Cavalcanti et al. | 604/4.01 |
| 2005/0274658 A1 * | 12/2005 | Rosenbaum et al. | 210/96.2 |
| 2006/0113250 A1 * | 6/2006 | Krensky et al. | 210/646 |
| 2006/0200064 A1 * | 9/2006 | Gross et al. | 604/5.01 |
| 2007/0023334 A1 * | 2/2007 | Hallstadius et al. | 210/94 |
| 2007/0131595 A1 * | 6/2007 | Jansson et al. | 210/96.2 |
| 2007/0209977 A1 * | 9/2007 | Wilf et al. | 210/85 |
| 2008/0010028 A1 * | 1/2008 | Mazon et al. | 702/30 |

FOREIGN PATENT DOCUMENTS

| | | | |
|---|---|---|---|
| EP | 0 658 352 A1 | | 6/1995 |
| WO | WO 03/066135 | * | 8/2003 |

* cited by examiner

METHOD FOR CONDUCTIVITY CALCULATION IN A TREATMENT FLUID UPSTREAM AND DOWNSTREAM A FILTRATION UNIT IN APPARATUSES FOR THE BLOOD TREATMENT

BACKGROUND OF INVENTION

The present invention relates to a method for conductivity calculation in a treatment fluid upstream and downstream a filtration unit in apparatuses for the blood treatment.

The invention also relates to a method for clearance and fistula flow determination using the above process for conductivity calculation.

It is known in the art to use conductivity measures for determination of parameters indicative of the filter efficiency during treatment, i.e. clearance or dialysance, and for determination of patient parameters, such as fistula flow.

EP 547025 shows a first method for determining clearance starting from a perturbation of the conductivity of the upstream dialysis liquid which creates corresponding response in the conductivity of the liquid downstream the dialysis unit.

Measures of the conductivity allow determination of downstream response and calculation of the clearance.

It is also known from EP 658352 an alternative method to calculate conductivity values for clearance calculation a short time perturbation.

It is also known to determine fistula flow by making a step like perturbation in the upstream conductivity and reversing the lines in the extracorporeal circuit during the step perturbation.

Measuring the conductivities in the spent dialysate across the flow reversal it is possible to arrive at fistula flow determination.

SUMMARY OF INVENTION

While the fistula flow calculation according to the above methods quite acceptable, it would be highly desirable to increase accuracy trying to reduce the time of the step like perturbation. More in general it is a goal of the invention to devise a method for conductivity determination in the spent dialysate upon a perturbation in the upstream liquid, increasing the accuracy, while keeping an acceptable measurement time.

It is also an aim of the present invention to render conductivity detections as much as possible independent from the step size, from the operating conditions and from the presence of undesired disturbances or noises.

These and other aims besides which shall be made clearer in the course of the following description, are substantially attained by a method for determining the conductivity of a treatment fluid downstream from a filtration unit in blood processing machines, as described in the accompanying claims.

BRIEF DESCRIPTION OF DRAWINGS

Further features and advantages will become more readily apparent from the detailed description of a preferred, but not exclusive, embodiment of a process for determining the treatment fluid conductivity according to the invention.

Such description shall be made hereafter with reference to the accompanying drawings, provided purely by way of non-limiting indication.

DETAILED DESCRIPTION

The present invention relates to a technique for determining the conductivity of a treatment fluid downstream from a filtration unit in blood processing machines and also describes one technique of calculating clearance and access flow.

The method is based on studying the dialysate outlet conductivity response that follows a rising of the dialysis solution conductivity and a shifting of the blood flow connections to the patient.

The response of a dialysis solution conductivity step is dependent on many factors. It is therefore difficult to extract the asymptotic components needed for calculation of the clearance.

This is true even more so for the access flow step, since the change in dialysate outlet conductivity, due to the reversal of the blood flow direction, is really small.

The algorithm described below has shown to be the one that gives the best results for both clinical data as well as data generated by a computer model.

The various variables used in the specification and in the claims later on are below defined in the table 1.

When relevant, the time interval from which data shall be extracted and processed for calculating the variable is given.

Figure 1:
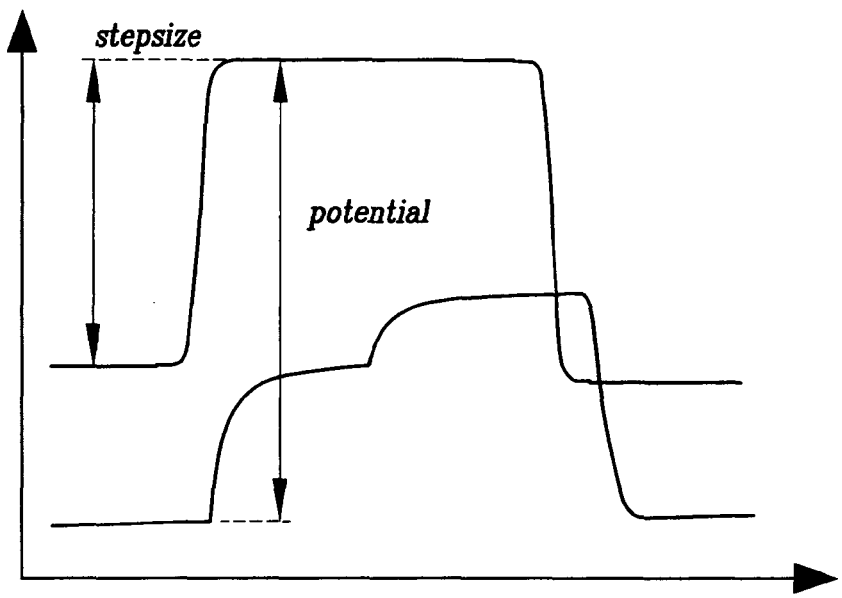
FIG. 1 shows the conductivity curves of the conductivity values upstream and downstream from the filtration unit in their time development.
Figure 2:
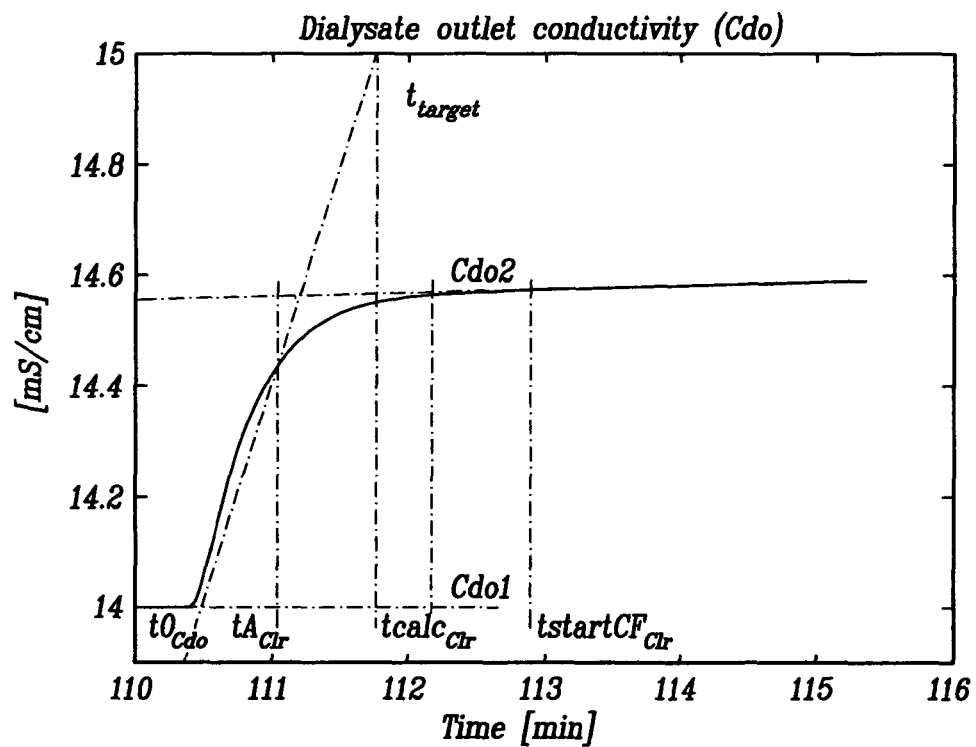
FIG. 2 shows a computer model generated curve of the dialysate outlet conductivity (Cdo)
Figure 3:
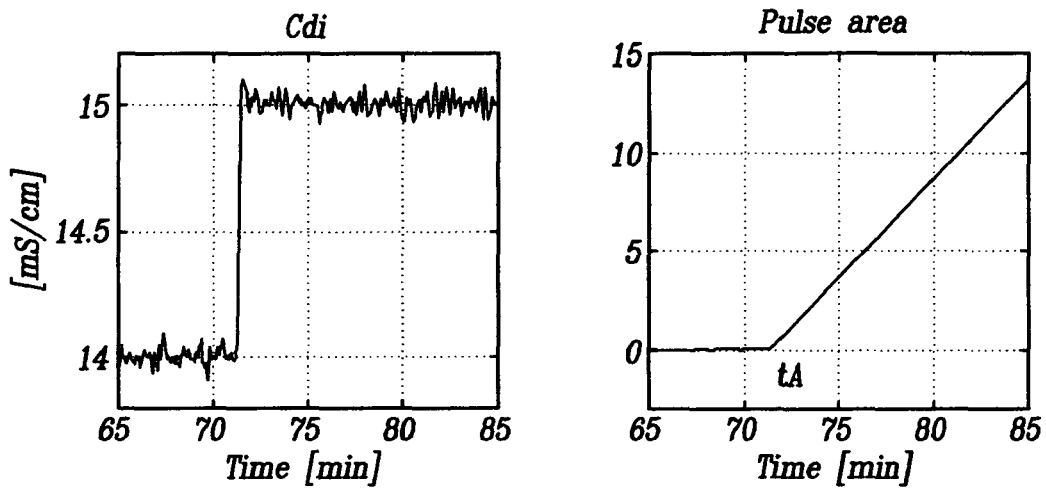
FIG. 3 shows real data dialysate inlet conductivity (Cdi)
Figure 9:
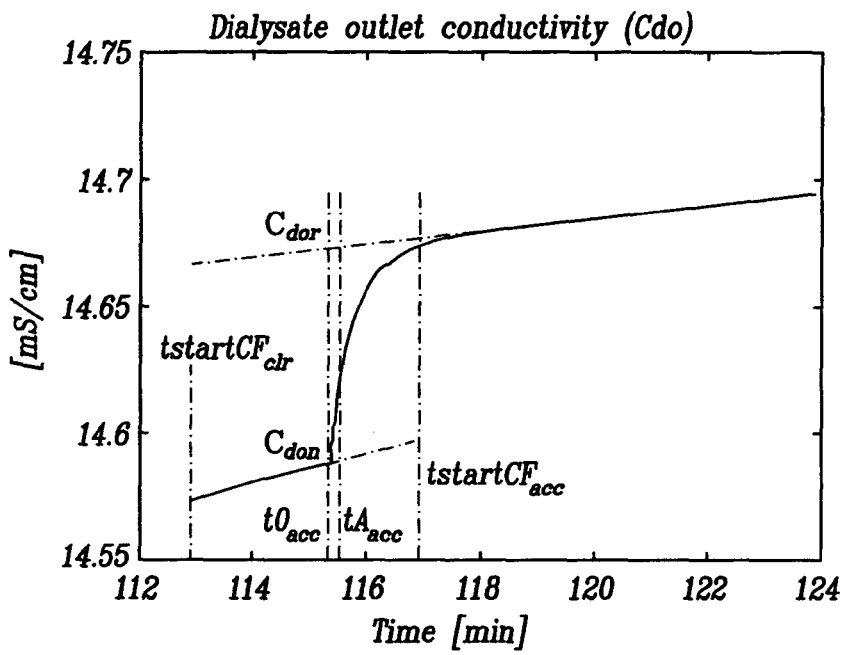
FIG. 9 shows the effect of the flow reversal in the dialysate outlet conductivity as a small step.

Some of the definition are also illustrated in FIG. 1, FIG. 2 and FIG. 9 as annexed.

TABLE 1

| Variable | Description | Data interval [minutes] | |
|---|---|---|---|
| | | Start point | End point |
| $K_e$ | Clearance (effective) | | |
| Cdi | Dialysis solution conductivity (dialyser inlet) | | |
| Cdi1 = $Cdi_{pre, mean}$ | Inlet pre step conductivity needed for the clearance calculation. | t0Cdi − (3 + $UF_{Cal}$_time) | t0Cdi − $UF_{Cal}$_time |

TABLE 1-continued

| Variable | Description | Start point | End point |
|---|---|---|---|
| $Cdi2 = Cdi_{step,\ mean}$ | Inlet step conductivity needed for the clearance calculation. | t0Cdi + 3 | tfCdi − 1 |
| $Cdi_{step,\ set}$ | The set value of Cdi during the condstep. | | |
| Cdo | Dialysate conductivity (dialyser outlet) | | |
| $Cdo_{corr}$ | Adjusted Cdo data. | $t0_{cdi} + 0.5$ | $tf_{cdi} - 0.5$ |

| | | Data interval | |
|---|---|---|---|
| Variable | Description | Start point | End point |
| Cdo1 | Outlet pre step conductivity needed for the clearance calculation. | | |
| Cdo2 | Outlet step conductivity needed for the clearance calculation. | | |
| $Cdo2_{est}$ | An estimation of Cdo2 taken at $t0_{Cdo}$. Used for adjusting data. | | |
| $Cdo_{pre,\ mean}$ | Outlet pre step conductivity mean value | t0Cdo − (3 + $UF_{Cal}$_time + Cdo_Cdi_delay) | t0Cdo − ($UF_{Cal}$_time + Cdo_Cdi_delay) |
| Cdon | Outlet pre reversal conductivity needed for the access flow calculation. | | |
| Cdor | Outlet post reversal conductivity needed for the access flow calculation. | | |
| $t0_{Cdi}$ | Calculated estimated time of when Cdi starts to raise. | | |
| | The area calculation, uses data between | 0.5 minutes before end of UF calibration. | Point when machine takes the Cdi down. |
| | The line fit is done on area data | 0.5 minutes after end of UF calibration | 1 minute prior to the end of the Cdi pulse |
| $tf_{Cdi}$ | Time when Cdi starts to drop back to normal. | | |
| $t0_{Clr}$ | Calculated estimated time of when Cdo starts to raise. | | |
| $UF_{Cal}$_time | The UF calibration takes some 45 seconds and is done prior to the raise in Cdi. Data during this period should not be used. Time set with a 15 seconds margin to 1 minute. | | |
| Cdo_Cdi_delay | How much Cdo is delayed ($t0_{Cdo} - t0_{Cdi}$) | | |
| $tCalc_{clr}$ | Time at which the conductivities Cdo1 and Cdo2 are taken | | |
| $tCalc_{acc}$ | Time at which the conductivities Cdon and Cdor are taken | | |

The following calculation method is particularly adapted for blood-treatment apparatuses having at least a filtration unit 10 with a first compartment 12 for the circulation of blood and a second compartment 14 for the circulation of the treatment fluid; the first and second compartments 12 and 14 are separated by interposition of at least a semi-permeable membrane 16 known in the art.

The machine also comprises means for changing the conductivity of the treatment fluid upstream from the filtration unit 10 such as a sodium reservoir 18 and a controlled pump 19 capable of injecting predetermined quantities of conductive fluid in the dialysate fluid up the filtration unit 10.

Obviously the treatment machine also comprises at least a first sensor 20 and a second sensor 22 for measuring, respectively, the conductivity of the process fluid upstream and downstream from the filtration unit 10.

A control unit 24 governs said devices in order to change the conductivity of the process fluid and is able to receive the conductivity signals from the aforementioned first and second sensors 20 and 22 allowing the calculation of the conductivity of the fluid as hereafter explained.

From a general point of view, after creating a flow of treatment fluid through the second compartment 14 of the filtration unit, a change in the conductivity of the treatment fluid at the inlet of the filtration unit 10 is imposed for a predetermined time interval.

The step in the Cdi curve is clearly shown in FIG. 1.

Such a step cause thereby an induced conductivity change in the fluid at the outlet of said filtration unit (see again FIG. 1—Cd0 curve).

After a predetermined time interval following the step in the inlet conductivity the blood flow to the fistula is reversed causing recirculation in the fistula and the consequent change in the conductivity curve downstream from the filtration unit (see the second step in the Cd0 curve—FIG. 1).

The method allows firstly to determine the conductivity value Cdo2 of the process fluid downstream from the filtration unit after the induced conductivity change used for clearance calculation and then allows to calculate also access flow.

Clearance is calculated by studying the first part of the step response curve. FIG. 2 shows a computer model generated curve of that part. The conductivity change imposed in the inlet fluid is a known change in value remaining constant over time, said change particularly being a positive change in conductivity (an increase in conductivity). The size of the step in the inlet conductivity is 1 [mS/cm] (from 14 to 15 [mS/cm]). The time points illustrated in the figure will be elucidated in the text below.

The measurement procedure is activated by the operator. Thereafter no changes to the treatment parameters are allowed in order to create stable conditions for the measurement. In a period of three minutes before the known Ultra filtration (UF) calibration, Cdo and Cdi-data are being collected. These data are necessary for the estimation of Cdo1 and Cdi1.

In connection to the UF-calibration, in fact at the end of it, a step in Cdi is initiated. After about 1 minute the response in Cdo is beginning show. After an additional time of 5 minutes the operator is prompted to reverse the blood flow direction to the patient. Should the operator not have reversed the flow within 2 minutes, the measurement should be aborted.

From the time when having reversed the blood flow direction, it again takes some 1 minute until the effects start to show in the Cdo-curve. Just before the effects start to show we have reached as far in the measurement as to plot the curve that is seen in FIG. 2. From this part of the curve, the effective clearance ($K_e$) can be calculated. The steps needed to obtain it, are described in the following part.

Fluctuations in Cdi create fluctuations in Cdo. Since we want to study the effects in Cdo of a raise in Cdi it would have been optimal if Cdi had been constant. Of course Cdi is not constant, but one way of "making it appear constant", is to compute the deviation that Cdi does from its mean value over the pulse, and then adjust the Cdo in proportion to it. Through this, we will expect a Cdo-curve close to the one we would have got if the response in Cdi had been equal to the actual pulse mean value.

To be able to perform this adjustment the two curves must be made synchronous. We therefore have to find the starting point of the curves and move one of them to the starting point of the other.

The synchronization process then allows to compare the conductivity curves upstream and downstream from the filtration unit after they have been synchronized in order thereby to determine one or more downstream conductivity values.

Finding the start of the Cdi pulse, is quite straightforward. It is done by assessing how the area under the step develops (should be an almost straight line), make a line fit to the pulse area "line" and see at what time it has its zero value ($tA_{Cdi}$). Since the Cdi curve goes up quite steeply, this time point corresponds to the sought starting point of the Cdi-curve ($t0_{Cdi}$).

In other words the characteristic time ($t0_{Cdi}$) of the upstream conductivity curve is calculated by estimating an area defining below the inlet conductivity curve; such a characteristic time is coincident with the instant at which the area under the curve takes on an average value greater than a predetermined threshold.

The point when Cdi goes back to normal, $tf_{Cdi}$, is also needed in the calculations later on. It could be found using the same technique as when finding $t0_{Cdi}$. $tf_{Cdi}$ is only used for referring of other time points. We can therefore equally well use the time when the machine goes back to the set value it had before the step.

The determination of the characteristic time $t0_{Cdo}$ of the conductivity curve downstream from the filtration unit comprises a step consisting in a preliminary estimation of the value of the characteristic time and the preliminary estimate is subsequently corrected.

When finding $t0_{Cdo}$ we basically fit a curve to the initial data of the Cdo step, and where this curve intersects with $Cdo_{pre}$ we find $t0_{Cdo}$.

Figure 4:
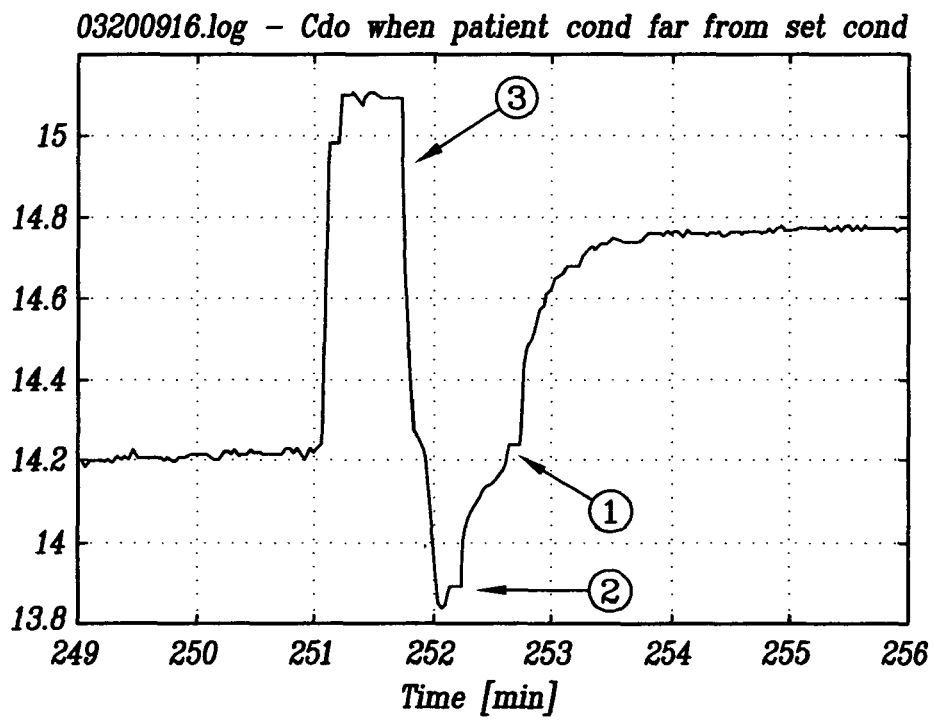
FIG. 4 shows a representation of the dialysate outlet conductivity curve when there is a big difference between the set conductivity and the patient conductivity.

FIG. 4 shows what the Cdo pulse may look like when there is a big difference between the set conductivity and the patient conductivity. The point $t0_{Cdo}$ is located somewhere at 1 but could easily be pointed out to lie at 2 if data are not carefully handled.

Prior to 3 a UF calibration was made. As can be seen, the UF calibration will result in a "bump". The bump might be quite big if, as in this case, there is a big difference between the patient conductivity and the set conductivity. What is shown here is quite extreme, but it shows an important case.

We know that the raise in conductivity is not made until the UF calibration is finished. This occurs when the bump is on its way downwards, i.e. at 3. Data prior to this point in time shall therefore not be used. We also know that it will take some minute before the raise in Cdi will start to show in Cdo. Therefore we can actually exclude another half a minute of data after the end of the UF calibration. We do not exclude the full 1 minute since we need to have some margin.

After any UF calibration there is always a "recoil effect", before Cdo returns to the course it had before the UF calibration. This means that we have some data, between 3 and 1 that should not be used either. If we do, we will, in the case described by FIG. 4, end up finding $t0_{Cdo}$ at 2. We must therefore confine the data to fulfill the condition $Cdo>Cdo_{pre}$ if the step is made upwards and $Cdo<Cdo_{pre}$ if the step is made downwards.

If the patient conductivity is larger than the set conductivity, the "bump" will go downwards and the recoil effect will accordingly go upwards. This means that the condition above is not enough. In this situation, when having followed the steps above, we would get Cdo-data that has a minimum at 1 (FIG. 4). Data prior to 1 will, if the bump is big, cause problems in the subsequent calculation of $t0_{Cdo}$. Therefore we need to exclude data prior to this point.

Figure 5:
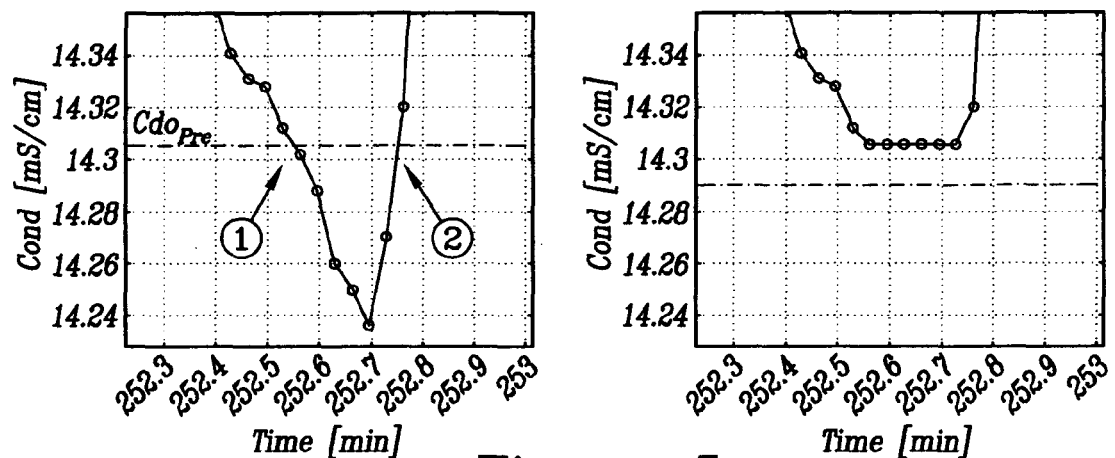
FIG. 5 shows a dialysate outlet conductivity curve part before the induced conductivity change.

By excluding these data we have almost solved the problem. We are however not there yet, since we might in fact get the minimum at the "wrong end". FIG. 5 (left) shows a situation where we have cut out a piece of the Cdo curve around the minimum. If the curve, after the recoil, passes $Cdo_{pre}$ a second time, the minimum might lie at 1 or 2 depending on how the sampling has been done. In the chosen example, the minimum will be found at 1, which is not what we want. We want 2.

We must therefore first check if there are any points lying below (or above if the step goes downwards) $Cdo_{pre}$. If so, we check which of them that has the latest time stamp. That one gives us the point we are looking for.

Furthermore, it can happen that all data are above $Cdo_{pre}$ as in FIG. 5 (right). Several "minimum values" might be found, e.g. if the same value has been recorded. Again the one with the latest time stamp gives us the point we are looking for.

The case described by FIG. 5 (left) could probably be excluded if one always performs the step according to the difference between Cdi and Cdo prior to the step. I.e. if Cdo<Cdi the step is done upwards. Downwards if Cdo>Cdi. However, before performing a step downwards one must think about what that might do to the patient. Lowering the sodium is considered "dangerous".

The data that now remains represents the step response and the very first data point of these data could, probably in most cases, with good enough result, be used as $t0_{Cdo}$.

In other words the preliminary estimation of the value of the characteristic time of the conductivity curve downstream from the filtration unit is made by determining the average conductivity at the outlet of the filtration unit $Cdo_{pre,mean}$ prior to the effects of the change in conductivity (the determination is made on the basis of an average, i.e. arithmetic mean, of the measured conductivity values Cdo prior to the effects of the change).

Subsequently the measured conductivity values are compared with previously determined average outlet conductivity value $Cdo_{pre,mean}$ and then the instant which measured the conductivity values Cdo that appear constantly greater than the previously calculated average outlet conductivity value $Cdo_{pre,mean}$ is estimated.

As above stated where the measured conductivity values Cdo exceed the average outlet conductivity value $Cdo_{pre,mean}$ a number of times, the preliminary estimate of the characteristic time $t0_{Cdo}$ of the conductivity curve downstream from the filtration unit, is the instant of the first condition in which the measured conductivity values Cdo are greater than the average outlet conductivity value $Cdo_{pre,mean}$.

We shall however undertake some "additional" steps to find an even better $t0_{Cdo}$ and therefore the step of correcting the preliminary estimate of the characteristic time may be performed.

Figure 6:
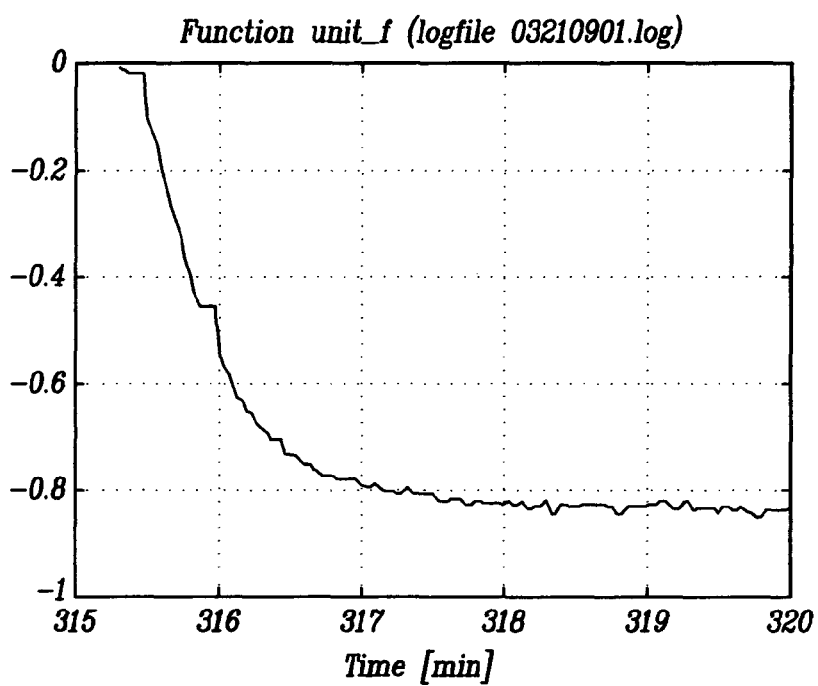
FIG. 6 shows a computer model representation of function unit_f.

We start by creating the natural logarithm function $f=\ln(\text{sign}*(Cdi_{step,set}-Cdo))$. The values of Cdo to use, are the ones starting at $t0_{Cdo}$ and extending up to the point in time when the reversion of the flow direction to the needles is done. Cdi is the step set value, $Cdi_{step,set}$, and not its actual values. The function f is scaled, by "potential", so that it corresponds to a unit step. We call the new function unit_f (unit_f=ln(sign*($Cdi_{step,set}$-Cdo)/potential)). The reason for scaling is of course that the calculations should be the same independently of the step size or how the patient conductivity relates to the set conductivity. FIG. 6 shows an example of unit_f.

Figure 7:
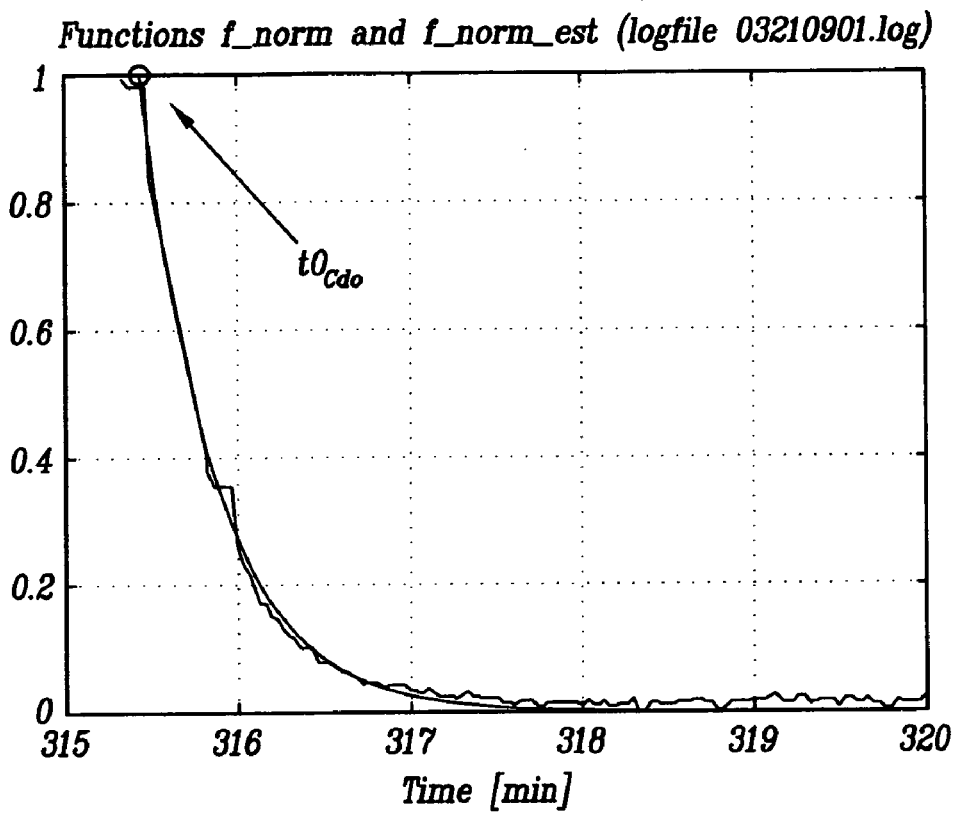
FIG. 7 shows a computer model representation of functions f_norm and f_norm_est.

We then make a least mean square line fit to function f between t=(tRev−1.5 minutes) and t=tRev. This range represents a part of the curve where the transients have died out. The estimation is called $Cdo\_1n_{clr}$ ($Cdo\_1n_{clr}=Cdi_{set,step}-\text{sign}*(\exp(c_{clr}(1)*t+c_{clr}(2)))$, $c_{clr}(1)$ and $c_{clr}(2)$ being the coefficients from the fit). We now construct a function $f2_{clr}=Cdo\_1n_{clr}-Cdo$ which express the short time behavior of the pulse. We standardize $f2_{clr}$ and get f_norm=($f2_{clr}$−min($f2_{clr}$))/max($f2_{clr}$−min($f2_{clr}$)). Again this procedure enables us to utilize the data independently of the curve form, potential and the step size. An example of the f_norm curve is shown in FIG. 7.

The next step is to make a least mean square line fit to ln(f_norm) in the range 0.2<f_norm<0.8, i.e. the initial part of the curve (different ranges might be used e.g. 0,1:0,9). An estimation of f_norm, f_norm_est, is then given by f_norm_est=exp($c_{clr}(3)*t+c_{clr}(4)$) where $c_{clr}(3)$ and $c_{clr}(4)$ are the coefficients generated by the line fit.

By having performed the selection of data as described above, we know that f_norm=1 corresponds to $Cdo=Cdo_{pre}$. This means that when f_norm_est equals the value 1 we are at what we define as $t0_{Cdo}$. $t0_{Cdo}$ is therefore easily calculated as $t0_{Cdo}=-c_{clr}(4)/c_{clr}(3)$.

We have now got the needed t0 values and can start adjusting the data. We start by synchronizing the two curves (i.e. moving the Cdo data so that $t0_{Cdo}$ coincide with $t0_{Cdi}$).

The mean value of Cdi during the step is calculated. To get the most appropriate mean value we use data between ($t0_{Cdi}$+3 minutes) and ($tf_{Cdi}$−1 minute). This excludes any overshoot effects and possible end effects and focuses on data being the base for the clearance and access flow estimations. The mean value is denoted $Cdi_{step,mean}$.

Also a value representing the pre step Cdo parameter is needed. We will here use a mean value of the data. It is denoted $Cdo_{pre,mean}$.

Figure 8:
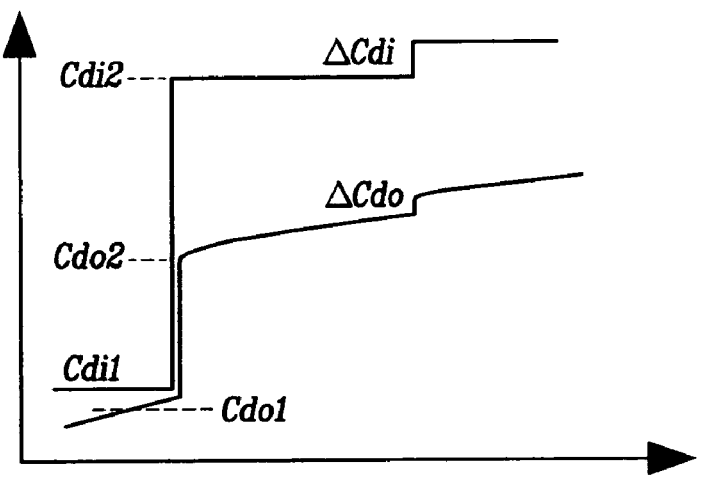
FIG. 8 shows a schematic representation of the dialysate inlet and outlet conductivity curve.

We are interested mainly in the big variations in Cdi and will therefore filter the signal quite hard. Only data between t=($t0_{Cdi}$+0.5 minutes) and t=($tf_{Cdi}$−0.5 minutes) is filtered. The filter used is an exponential one, $Cdi_{filt,i}=(N-1)/N*Cdi_{filt,j-1}+1/N*Cdi_{i-1}$. The filter factor N used for the used data is between 150 and 250 and in detail 200. The mean sampling interval for these data is between 0.01 and 0.1 and in detail 0.033 minutes, which corresponds to a time constant of about 6.6 minutes. As start value for the filter we use $Cdi_{step,set}$. The difference $Cdi_{diff}=Cdi_{filt}-Cdi_{step,mean}$ is created. A variation ($\Delta Cdi$) around the mean value is believed to give raise to a corresponding variation in Cdo ($\Delta Cdo$), see the simplified case shown in FIG. 8. Such a variation in Cdi can be seen as a small step in the inlet conductivity and shall, governed by the clearance, give a corresponding variation in Cdo. We assume therefore that the following is true: (raise in Cdo (Cdo2−Cdo1) due to raise in Cdi)/(raise in Cdi (Cdi2−Cdi1))=(variation in Cdo ($\Delta Cdo$))/(variations in Cdi ($\Delta Cdi$)). This gives us the corrected Cdo values as: $Cdo_{corr}=Cdo+(Cdo2-Cdo_{pre,mean})*Cdi_{diff}/\text{step size}$. Here we encounter a small problem. The value of Cdo2 will not be known until we are ready to calculate the clearance. Therefore we use an estimate of it, called $Cdo2_{est}$, which is the value that the above assessed function $Cdo\_1n_{clr}$ gives at $t=t0_{Cdo}$. Another problem is that the correction is actually only valid when the needles are in the normal position. In the reverse position the clearance is lower and the correction should hence have been somewhat smaller. Since the difference between $K_n$ and $K_r$ is quite small and since we are discussing only the correction, which is small, we assume that the error we introduce is very small.

Now that we have adjusted the data the method further comprises a step of consisting in mathematical computation of the conductivity curve downstream from the filtration unit in order thereby to determine a characteristic time tStartCF beyond which the conductivity curve has stabilized after undergoing the effects of the imposed change in conductivity. Said characteristic time tStartCF is given by the sum of two terms, a first term $t_{target}$ which is function of the conductivity curve and a second term tcbf which is function of the blood flow.

In determination of the first term $t_{target}$ for calculating the characteristic time we first estimate an intermediate time $tA_{clr}$ and we then derive the first term $t_{target}$ as following explained.

We will firstly obtain what we call $tA_{clr}$ which is a time representative of the effects of the transient due the conductivity change in the upstream liquid. Indeed $tA_{clr}$ depends upon several factors among which we can mention the filter volume, blood and dyalisis liquid flows, the conductivity step and so on depending on which $tA_{clr}$ moves near or far from the terminal instant of the transient. For obtaining $tA_{clr}$ we use $Cdo_{corr}$ data between $t0_{Cdo}$ and tRev. The procedure is similar to what was described for finding $t0_{Cdi}$ but instead of trying to find a "baseline" towards which the area under $Cdo_{corr}$ should be created we instead use the function unit_f above. The area referred to is therefore the one restrained by unit_f and the t-axis. We make a least mean square fit to the area data in the interval t=(tRev−1.5 minutes) and t=tRev. $tA_{clr}$ is then defined as the point where the line crosses the t-axis, i.e. where the line has its zero value. Since the area function is nice, i.e. very little noise, one could (to get less calculations) instead of making a least mean square fit, use a line going through the endpoints of the interval.

The next step is to construct a line going through the points ($t0_{Cdo}$, Cdo0) and ($tA_{clr}$, CdoA), see FIG. 2. This line is extrapolated to a conductivity equal to $Cdo_{pre}$+step size. The time point then obtained is called $t_{target}$. Where, in time, this point is located, compared to $t0_{Cdo}$, is dependent on the shape of the curve, i.e. the dialyser used, blood flow, dialysis solution flow and also parameters origin from the patient. It expresses a sort of time constant for the curve.

To $t_{target}$ we will add a time, dependent on the blood flow (tcbf=16/60+260/Qb). The reason is that it is shown by the modeling work that the concentration in the body, Cvv (venous blood concentration), develops with a time delay of this size. This time is, since it is based on the blood flow, also linked to the shape of the Cdo curve. In the modeling work, the time used was about 1 minute. Also for clinically recorded data 1 minute was a good choice.

The time tcbf has two uses. The first is adding it to $t_{target}$. By that, we will get to a position on the Cdo curve where most of the initial effects have decayed. The time point obtained (tstartCF) is the one from which we start using Cdo data for the subsequent estimation. The second use is for finding the best time for the clearance calculation (see below).

We choose to make the line fit to data between t=tstartCF$_{clr}$ and t=(tstartCF$_{clr}$+1.5 minutes). We assume that, by using a fixed range relative to tstartCF$_{clr}$, we are using data from the same part of the curve independently of whatever parameters having influenced the curve. The line fit is the same as described above, i.e. we create the function f=ln(sign* (Cdi$_{step,mean}$−Cdo$_{corr}$)) and make a least mean square fit to it. Observe that the Cdi used is now the step mean value of Cdi. As before we create Cdo_ln$_{clr}$=Cdi$_{step,mean}$−sign*exp(c(1) *t+c(2)), where c(1) and c(2) are the coefficients from the fit. The function Cdo_ln$_{clr}$ will then give us the sought Cdo2 needed for the clearance calculation.

Should it not be possible to use data up to t=(tstartCF$_{clr}$+1.5 minutes) for the curve fitting, i.e. tRev is passed, the rise is considered to slow and no calculation should be performed. The operator should be informed about it and what actions to take. The clearance (effective) is calculated through the expression:

$$K_e = (Q_d + Q_{UF}) \cdot \left(1 - \frac{Cdo2 - Cdo1}{Cdi2 - Cdi1}\right)$$

where Cdi2 is equal Cdi$_{step,mean}$ (alternatively also the set values Cdi$_{set,step}$ may be used) and Cdi1 is equal to Cdi$_{pre,mean}$ (alternatively also the set values Cdi$_{set,pre}$ may be used); it is also clear that, due to the symmetry of the clearance calculation expression, values of both Cdi2 and Cdi1, Cdo2 and Cdo1 may be inverted.

Cdo2 is the value that Cdo_ln$_{clr}$ gives at t=tCalc$_{clr}$=tA$_{clr}$+ tcbf.

Cdo1 is given by function Cdo$_{pre}$, extended and taken at tCalc$_{clr}$. Cdo$_{pre}$ is created by performing a line fit to Cdo data in the same interval as is used when assessing Cdo$_{pre,mean}$. One may wonder why we are not creating and using an exponential function also for these data, but the reason is that it is difficult when Cdo and Cdi are close in value. Qd and Quf are the flow rates of the dialysis solution and the UF respectively.

Above is described the case where a fixed time of 1.5 minutes is used for fitting a curve to Cdo-data in order to get Cdo2. This gives, as an average, a better value on the effective clearance Ke. However, from a standard deviation of Ke point of view (if possible), it could perhaps be better to use as much data as possible from the step. If this is done we need however to move the calculation point somewhat towards the left since the whole curve and hence also Cdo2 otherwise becomes a bit too high.

Figure 12:
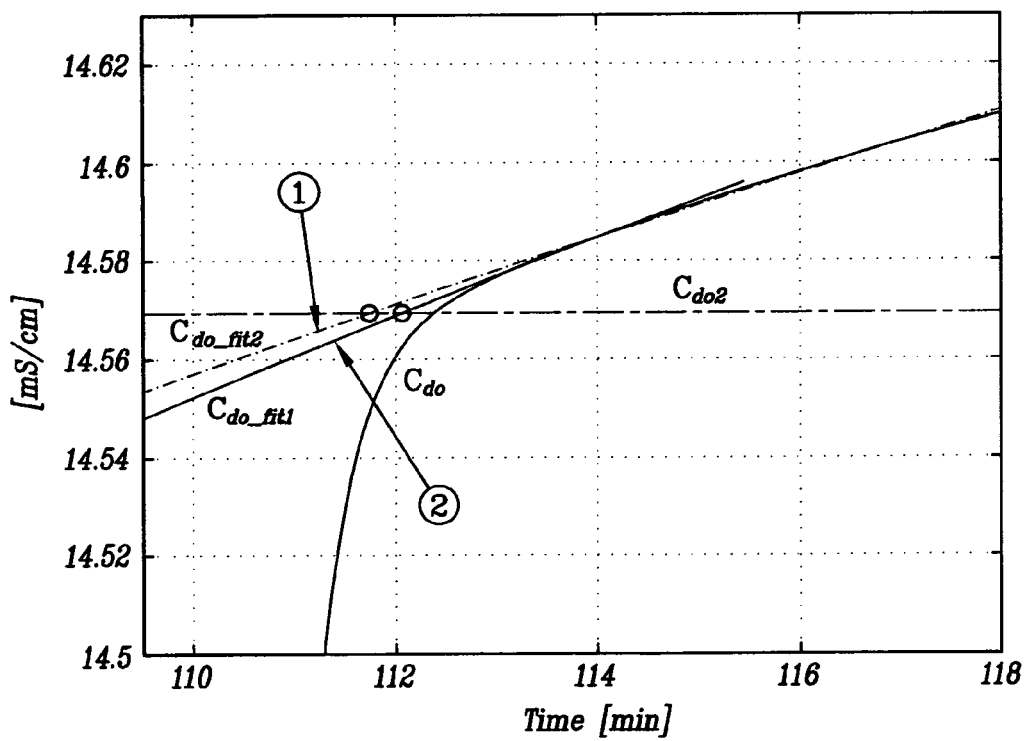
FIG. 12 shows two different line fits made to the Cdo curve.
Figure 13:
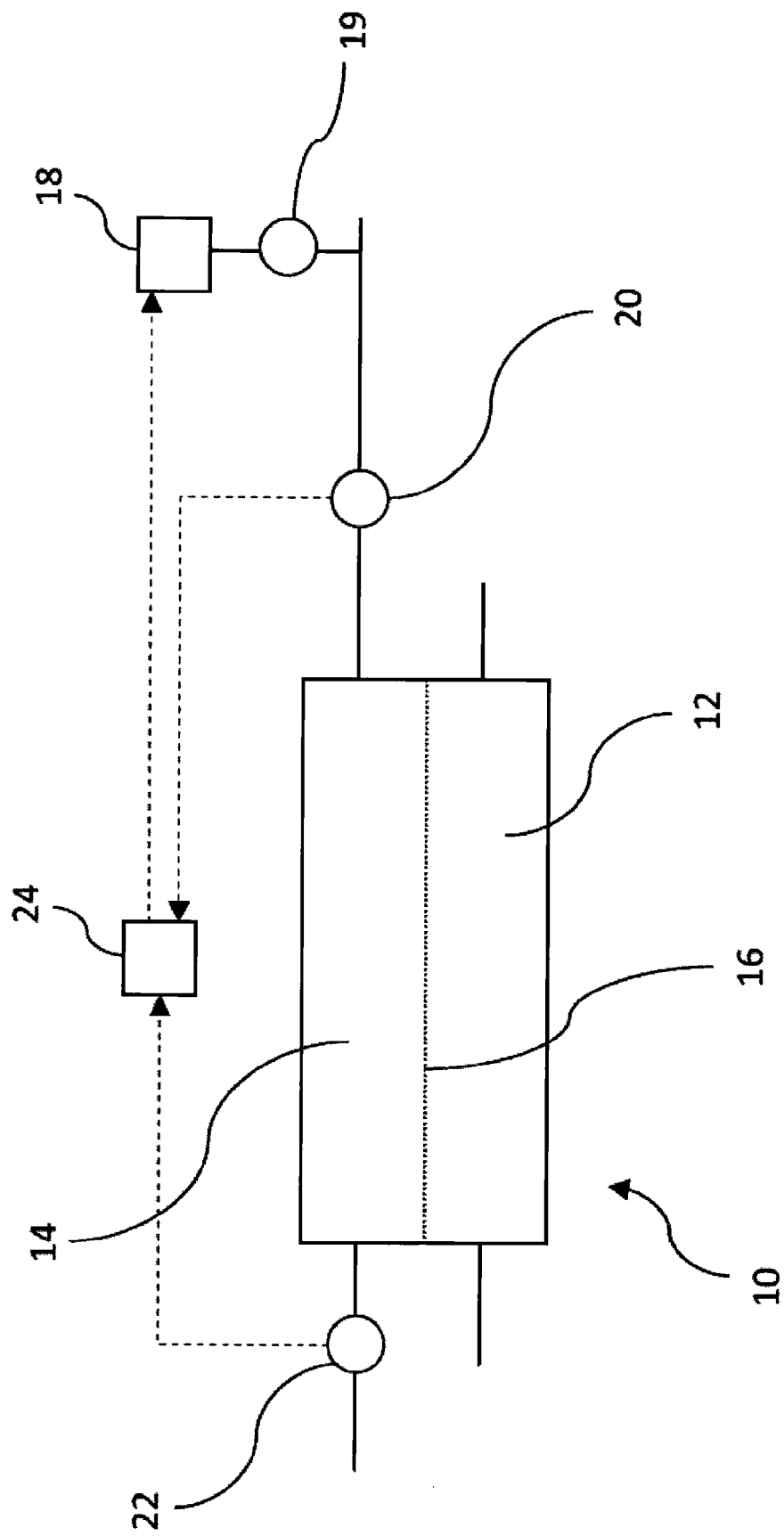
FIG. 13 shows a blood treatment machine.

As shown in FIG. 12 two line fits have been made to the Cdo curve, Cdo_fit1 and Cdo_fit2 when creating Cdo_fit1 we used data of an interval of 1.5 minutes; viceversa the line fit according to Cdo_fit2 required an interval of 5 minutes (i.e. more data have been used). As can be seen the Cdo_fit2 curve is then lifted some (1) and hence giving somewhat higher conductivity values. Also the horizontal line Cdo2 has been drawn.

Assuming that we got the conductivity value Cdo2 from the first line fit at time t=112.1 min, to get the same Cdo2 value from the second line fit we need to move towards the left, to t=118 min.

In the real case, if, for stability reason, we would choose to use more data this would represent the second curve fit. Consequently we should move the calculation point to the left. One choice is to use $t0_{Cdo}$; this is of course not the proper point but it is one that is already in the algorithm.

The access flow is calculated from the step one get when shifting the blood flow to the needles, i.e. blood taken out upstream is shifted with blood entering downstream. This creates a recirculation in the fistula, which affects the efficiency of the dialysis. $K_e$ becomes less. How much the flow reversal reduces the efficiency is dependent on the access flow. The effect of the flow reversal is seen in the Cdo-curve as a small step (FIG. 9). The size of the step, along with the clearance gives the access flow.

The procedure for the access step calculations could theoretically be the same as for the clearance step. However, the noise is making this approach difficult since this step is much smaller than the clearance one. Therefore we need to do somewhat differently. We are going to describe two ways of finding the parameters needed. One that gives a more correct point for calculation of the access flow, but which might result in a larger variation. The second approach gives results which are the other way around.

The method for calculating fistula flow generally comprises the step of determining the filter clearance as above described, when reversing the blood flow direction to the fistula and determining, by means of mathematical calculation, an outlet conductivity prior the reversal of the blood flow Cdon; furthermore the method includes the step of determining a conductivity of the outlet process fluid Cdor following the reversal in blood flow and setting or estimating an inlet conductivity Cdi after the imposition of a change in conductivity.

If the switching of the blood flow to the fistula is made manually one should choose $t0_{acc}$ as the point in time at which the conductivities for the access flow calculation, should be taken. When shifting manually, an overshoot in $C_{do}$ is induced. Dependent on how the shift is done (e.g. how long it takes) the overshoot will vary from time to time. $t0_{acc}$ is independent of how the shifting is done. Therefore, the variations in $Q_a$ become less. As in the clearance step, the correct time lies some time after $t0_{acc}$.

We want our method to find consistent values of $t0_{acc}$ independently of if the reversion is made manually or automatically. Since the Cdo curve, in these two cases, behave differently; the method of using the area does not lead to this consistency. Therefore, the route of using the "derivative" has been chosen.

One problem of using derivatives of signals is that they usually become noisy. The first action is therefore to filter $Cdo_{corr}$. The variable is called Cdo_flt. The same filter as described above is used. The difference is that the N is now 20 (with a sample time of 0.033 min this reflects a time constant of about 40 seconds).

We create the function f_flt=ln(sign*($Cdi_{step,mean}$−Cdo_flt)) and make a least mean square line fit to it between the time points t=(tfCdi−4 minutes) and t=(tfCdi−1 minute). This range represents a part of the curve where the transients have died out. The fit gives us an estimation of the of Cdo curve called $Cdo\_ln_{acc,est}$ ($Cdo\_ln_{acc,est}$=$Cdi_{step,mean}$−sign*exp($c_{acc,est}(1)$*t+$c_{acc,est}(2)$), $c_{acc,est}(1)$ and $c_{acc,est}(2)$ being the coefficients from the fit). We now construct a function $f2_{acc}$=$Cdo\_ln_{acc,est}$−Cdo_flt, which express the short time behavior of the pulse. Further we derive the difference function of $f2_{acc}$ i.e. $diff\_f2_{acc}$=$f2_{acc}(i)$−$f2_{acc}(i-1)$, i being the sample number. Standardizing $diff\_f2_{acc}$ gives us the standardized derivative of $f2_{acc}$, $f2_{der\_norm}$=$diff\_f2_{acc}$/min ($diff\_f2_{acc}$). The function ranges from 0 to 1. In $f2_{der\_norm}$ we search for the point in time when the value for its first time becomes >0.5 (called $t0_{acc,est}$). By having filtered the data, Cdo_flt is somewhat delayed compared to the original Cdo data. Therefore, we make an adjustment of $t0_{acc,est}$ and get $t0_{acc}$=$t0_{acc,est}$−0.1 minute.

By using the $f2_{acc}$ function also on its way downwards one could get a better estimate of when the transients have died out. This means that we can find a good estimate of when to start using data for the line fit of $Cdo_{corr}$ during the reverse flow period. The point we are going to search for is the one obtained when $f2_{der\_norm}$, after having passed its maximum, gets below 0.2. This point in time plus a margin of 0.5 minutes gives us the time t=$tstartCF_{acc}$.

How the access flow is calculated is described below.

If the switching of the blood flow to the fistula is made automatically, a somewhat better point in time to use for the access flow calculation is $tA_{acc}$.

$tA_{acc}$ is derived in the same way as was $tA_{clr}$. We create the function unit_f for data between $t0_{acc}$ and $tf_{Cdi}$−1 minute (unit_$f_{acc}$=ln(sign*($Cdi_{step,mean}$−$Cdo_{corr}$)/potential)). We derive the area function. The area referred to is the one restrained by unit_$f_{acc}$ and the t-axis. We then make a least mean square fit to the area data in the interval t=$tstartCF_{acc}$ and t=$tf_{cdi}$−1 minute. $tA_{acc}$ is then defined as the point where the line crosses the t-axis, i.e. where the line has its zero value.

Figure 10A:
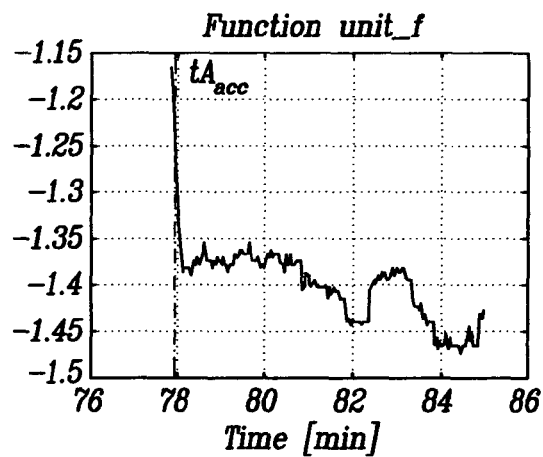
FIG. 10a shows a representation of function unit_$f_{acc}$.
Figure 10B:
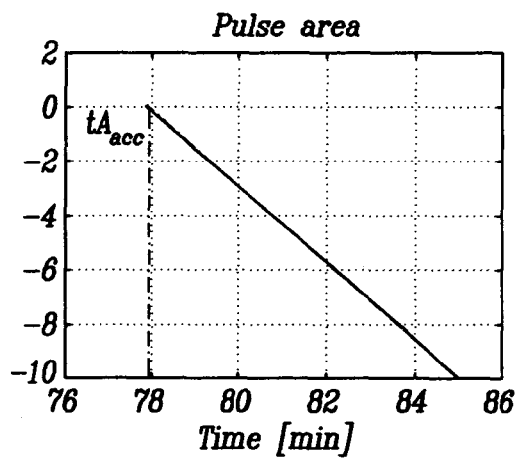
FIG. 10b shows the area associated to function unit_$f_{acc}$.

In FIG. 10 are shown example plots of unit_$f_{acc}$ and the associated area.

Figure 11:
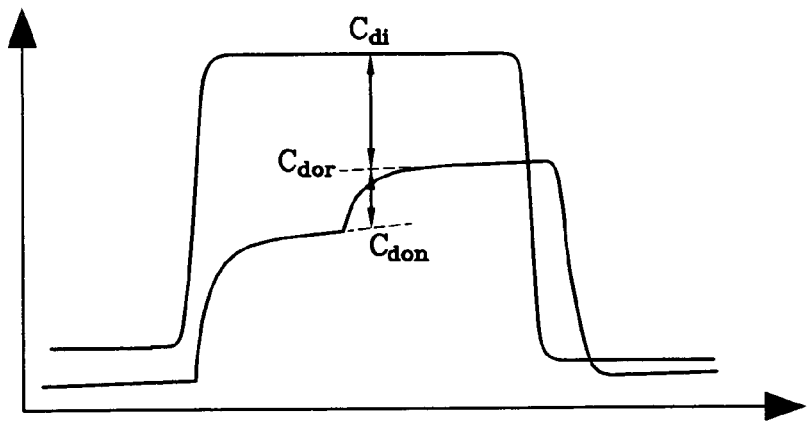
FIG. 11 again shows the inlet and outlet conductivity curves and relevant steps used for calculating access flow.

The access flow is calculated using the expression $$Q_{aw} = (K_e + Q_{UF}) \cdot \left( \frac{Cdor - Cdi}{Cdon - Cdor} \right)$$

where $K_e$ is the effective clearance obtained as above. $Q_{uf}$ is the UF. The conductivities are best described by FIGS. 9 and 11.

To get the values of the conductivities we create the function f in the same way as for the clearance step. We make a least mean square line fit to the function for data lying between t=$tstartCF_{acc}$ and t=$tf_{cdi}$−1 minute. The resulting Cdo estimation then becomes $Cdo\_ln_{acc}$=$Cdi_{step,mean}$−sign*exp($c_{acc}(1)$*t+$c_{acc}(2)$), $c_{acc}(1)$ and $c_{acc}(2)$ being the coefficients from the fit. We do the same thing for the curve prior to the reversion. For this we use data between t=$tstartCF_{clr}$ and t=($t0_{acc}$−0.5 minutes). As result we get $Cdo\_ln_{pre,mean}$−sign*exp($c_{pre,acc}(1)$*t+$c_{pre,acc}(2)$).

Dependent on the situation of manual or automatic reversion of the blood flow, as described above, we use $tA_{acc}$ or $t0_{acc}$ as time point of when the conductivities are to be taken (=$tCalc_{acc}$). $Cdo\_ln_{pre,acc}$ gives, at t=$tCalc_{acc}$, Cdon. $Cdo\_ln_{acc}$ gives at the same time point Cdor. Cdi is given by $Cdi_{step,mean}$.

The access flow that has now been calculated is the blood water access flow $Q_{aw}$. What we want is the whole blood access flow. With help from the book "Replacement of renal function by dialysis", fourth edition, chapter 2, page 41 one can set up the following expression for the conversion:

$$Q_a = \frac{Q_{aw}}{\left[ \left(1 - \frac{Hct}{100}\right) * \left(1 - \frac{Tp}{1000}\right) + \frac{Hct}{100} * Fr \right]}$$

were Hct is the hematocrit, Tp is the total plasma protein content and Fr is the red cell water fraction (volume water in red cells/total volume of red cells). If we use average values for the different quantities (Hct=35%, Tp=70 g/l and Fr=0.72) the expression becomes $Q_a$=1.168*$Q_{aw}$.

The invention achieves important advantages.

First of all it is to be noted that the method for determining the conductivity according to the present invention allows to increase the accuracy of calculation of clearance and of access flow.

The method is adapted to be used with different blood treatment machines and gives good results for different patients in different conditions.

In other words the method is general.

The present method allows also to more accurately access a conductivity needed for calculation of the clearance and of access flow by giving better estimation of the time point when the transition effect starts and ends.

Finally the conductivity detections are as much as possible independent from the step size, the operating conditions and from the presence of undesired disturbances or noises.

The invention claimed is:

1. A method for determining a conductivity of a treatment fluid downstream from a filtration unit in a blood processing machine, said unit comprising a first compartment for the circulation of blood and a second compartment for the circulation of the treatment fluid, said second compartment being separated from the first compartment by interposing at least a semi-permeable membrane; said method comprising the steps of:

creating a flow of blood through the first compartment of the filtration unit;

creating a flow of treatment fluid through the second compartment of the filtration unit;

imposing, for a predetermined time interval, a change in the conductivity of the treatment fluid at an inlet of the filtration unit to cause an induced conductivity change in the fluid at an outlet of said filtration unit;

measuring a predetermined number of conductivity values Cdo downstream from the filtration unit, said conductivity values Cdo defining a downstream conductivity curve;

defining at least one interpolating mathematical function for estimating a pattern of said downstream conductivity curve in an interval of time after causing the induced conductivity change;

wherein the mathematical function has the form:

$$Cdo\_ln_{cir} = Cdi_{step,mean} - \text{sign} * \exp(c(1) * t + c(2))$$

where c(1) and c(2) are coefficients derived from the least squares interpolation of the mathematical function and $Cdi_{step,mean}$=an inlet conductivity value after the change in conductivity;

determining a characteristic measuring time $tCalc_{clr}$, wherein said determination of said characteristic measuring time $tCalc_{clr}$ comprises the sub steps of estimating an intermediate time $tA_{clr}$ representative of a transient due to the induced conductivity change in the fluid, and correcting the intermediate time $tA_{clr}$ through an addition of a second time term tcbf, which is a function of the blood flow; and calculating by means of a control unit a value of the interpolating mathematical function at said characteristic measuring time $tCalc_{clr}$, said value representing a conductivity value Cdo2 of the fluid downstream from the filtration unit after the induced conductivity change, wherein the determination of the characteristic measuring time $tcalc_{clr}$ comprises the following sub steps:

estimation of the intermediate time $tA_{clr}$ representative of a transient due to the induced conductivity change in the fluid, said time $tA_{clr}$ depending on at least a filtration unit volume, blood and treatment fluid flows, and the change in the conductivity of the treatment fluid at the inlet of the filtration unit, and correction of the intermediate time $tA_{clr}$ through the addition of the second time term tcbf, which is a function of blood flow rate, $tcalc_{clr}$ being defined as $tcalc_{clr}=tA_{clr}+tcbf$, the Cdo2 value being the value of the equation at $t=tcalc_{clr}$.

2. A method according to claim 1, wherein the conductivity change imposed in the inlet fluid is a known change in value remaining constant over time, said conductivity change being a positive change in conductivity.

3. A method according to claim 1, wherein the characteristic measuring time $tCalc_{clr}$ is calculated using the equation: $tCalc_{clr}=tA_{clr}+tcbf$, where $tcbf=16/60+260/Qb$, Qb being the blood flowrate.

4. A method according to claim 1, wherein the intermediate time $tA_{clr}$ is calculated using the function: unit_f=ln(sign*($Cdi_{step,set}$−Cdo)/potential), where potential=$Cdi_{step,mean}$−$Cdo_{pre,mean}$, and by performing an interpolation with a least squares estimation on the data of the area falling between said function and the x-coordinate time axis in a predetermined time interval, said intermediate time $tA_{clr}$ coinciding with the instant at which the interpolating function intersects the x-coordinate time axis.

5. A method according to claim 4, wherein the predetermined time interval for the least squares estimation of the function unit_f falls between a first instant of reversal in the blood line (tRev−1.5 min) and a second instant of reversal in the blood line tRev.

6. A method according to claim 1, further comprising the steps of:

measuring a predetermined number of conductivity values upstream from the filtration unit, said conductivity values defining an upstream conductivity curve;

determining a characteristic time $t0_{Cdo}$ of the downstream conductivity curve;

determining a characteristic time $t0_{Cdi}$ of the upstream conductivity curve;

synchronizing said downstream and upstream conductivity curves on the basis of the characteristic time of the downstream conductivity curve $t0_{Cdo}$ and the characteristic time of the upstream conductivity curve $t0_{Cdi}$, to enable comparison of the respective conductivity values; and comparing the downstream and upstream conductivity curves after the conductivity curves have been synchronized to determine one or more downstream conductivity values.

7. A method according to claim 6, wherein the characteristic time $t0_{Cdi}$ of the upstream conductivity curve coincides with the instant at which the change in conductivity occurs in the upstream conductivity curve, the characteristic time $t0_{Cdo}$ of the downstream conductivity curve corresponding to the instant at which the induced conductivity change downstream from the filtration unit occurs.

8. A method according to claim 7, wherein the characteristic time $t0_{Cdi}$ of the upstream conductivity curve is calculated by estimating an area defined below the upstream conductivity curve, the characteristic time $t0_{Cdi}$ coinciding with the instant at which the area under the upstream conductivity curve takes on an average value greater than a predetermined threshold.

9. A method according to claim 7, wherein the determination of the characteristic time $t0_{Cdo}$ of the downstream conductivity curve comprises a further step of making a preliminary estimate of the value of the characteristic time $t0_{Cdo}$ and subsequently correcting the preliminary estimate if incorrect.

10. A method according to claim 9, wherein the preliminary estimate of the value of the characteristic time of the downstream conductivity curve comprises the following sub steps: determining the average conductivity at the outlet of the filtration unit $Cdo_{pre,mean}$ prior to the effects of the change in conductivity, said determination being made on the basis of an average of the measured conductivity values Cdo prior to the effects of the change; comparing the measured conductivity values at the outlet of the filtration unit Cdo with the average outlet conductivity value $Cdo_{pre,mean}$; estimating the instant at which the measured conductivity values Cdo appear constantly greater than the average outlet conductivity value $Cdo_{pre,mean}$.

11. A method according to claim 10, wherein the measured conductivity values Cdo exceed the average outlet conductivity value $Cdo_{pre,mean}$ a number of times, causing the preliminary estimate of the characteristic time $t0_{Cdo}$ of the downstream conductivity curve to coincide with the instant of the last condition in which the measured conductivity values Cdo are greater than the average outlet conductivity value $Cdo_{pre,mean}$.

12. A method according to claim 9, wherein the step of correcting the preliminary estimate of the characteristic time $t0_{Cdo}$ value of the downstream conductivity curve comprises the following sub steps: creating an appropriate mathematical expression unit_f, which is a function of the conductivity values measured downstream from the filtration unit Cdo, and of the known change in the conductivity of the inlet fluid, $Cdi_{step,set}$, said expression being normalized if necessary; and, performing a least squares estimation of said expression unit_f in a predetermined time interval.

13. A method according to claim 12, wherein the mathematical expression is calculated by the following equation: unit−f=ln(sign*($Cdi_{step,set}$−Cdo)/potential)), where potential=$Cdi_{step,set}$−$Cdo_{pre,mean}$; $Cdi_{step,set}$=value of the known change in conductivity at the filtration unit inlet; Cdo=conductivity values measured downstream from the filtration unit; $Cdi_{step,mean}$=inlet conductivity value after the change in conductivity, and $Cdo_{pre,mean}$=average outlet conductivity value prior to the change in conductivity.

14. A method according to claim 13, wherein the least squares estimation is performed on the mathematical expression unit_f and the estimate is calculated by the following equation: $Cdo\_ln_{clr}=Cdi_{step,set}$−sign*(exp($c_{clr}$(1)*t+$c_{clr}$ (2))), where $c_{clr}(1)$ and $c_{clr}(2)$ are coefficients derived from the least squares interpolation of the mathematical expression unit_f.

15. A method according to claim 12, wherein the step of correcting the preliminary estimate of the value of the characteristic time of the downstream conductivity curve comprises the additional sub steps of: creating a mathematical function f_norm, which is a function of coefficients $c_{clr}(1)$ and $c_{clr}(2)$ derived from the previous least squares interpolation, and a function of the known change in conductivity $Cdi_{step,set}$ of the inlet fluid and a function of the conductivity values downstream from the filtration unit Cdo, said mathematical function f_norm being normalized if necessary; and, performing a least squares interpolation on the mathematical function f_norm within a predetermined interval of values.

16. A method according to claim 14, wherein the step of correcting the preliminary estimate of the value of the characteristic time of the downstream conductivity curve comprises the additional sub steps of: creating a mathematical function f_norm, which is a function of coefficients $c_{clr}(1)$ and $c_{clr}(2)$ derived from the previous least squares interpolation, and a function of the known change in conductivity $Cdi_{step,set}$ of Cdi the inlet fluid and a function of the conductivity values downstream from the filtration unit Cdo, said mathematical function f_norm being normalized if necessary; and, performing a least squares interpolation on the mathematical function f_norm within a predetermined interval of values, wherein the mathematical function used is calculated using the following equation: f_norm=(f2$_{clr}$−min(f2$_{clr}$))/max(f2$_{clr}$−min(f2$_{clr}$)), where f2cir=Cdo_1n$_{clr}$−Cdo.

17. A method according to claim 15, further comprising the sub step of creating a mathematical estimation function f_norm_est, which is a function of coefficients $c_{clr}(3)$ and $c_{clr}(4)$ derived from the least squares interpolation of the mathematical function.

18. A method according to claim 15, wherein the predetermined interval of values for performing the least squares interpolation on the mathematical function f_norm is between 0.1 and 0.9.

19. A method according to claim 17, wherein the corrected value $t0_{Cdo}$ of the characteristic time of the downstream conductivity curve coincides with the instant at which the mathematical estimation function f_norm_est takes on a value of 1.0.

20. A method according to claim 17, wherein the mathematical estimation function is calculated using the following equation: f_norm_est=exp($c_{clr}(3)$*t+$c_{clr}(4)$), where $c_{clr}(3)$ and $c_{clr}(4)$ are a coefficients derived from the least squares interpolation of the natural logarithm of the mathematical function f_norm.

21. A method according to claim 20, wherein the corrected value of the characteristic time $t0_{Cdo}$ is obtained using the following formula: $t0_{Cdo}$=−$c_{clr}(4)$/$c_{clr}(3)$.

22. A method according to claim 12, wherein the predetermined time interval of the mathematical expression unit_f in which the interpolation is to be performed essentially falls between a first instant of reversal in the blood line (tRev−1.5 minutes) and a second instant of reversal in the blood line tRev.

23. A method according to claim 6, wherein the step of synchronizing the upstream and downstream conductivity curves entails a relative translation between the upstream and downstream conductivity curves, ascribed a value D, D being a function of the characteristic times $t0_{Cdi}$ and $t0_{Cdo}$ determined by the upstream and downstream conductivity curves.

24. A method according to claim 1, further comprising the step of determining average inlet conductivity after the imposed change in conductivity $Cdi_{step,mean}$, said determination being based on an average of the measured conductivity values Cdi after the effects of the imposed change in conductivity.

25. A method according to claim 24, wherein the conductivity values Cdi used to determine the average inlet conductivity after the change in conductivity $Cdi_{step,mean}$ fall within a time interval between an instant at which a change in conductivity occurs in an upstream conductivity curve, $t0_{Cdi}$+3 minutes, and an instant at which the effects of a change in conductivity cease in the same curve, $tf_{Cdi}$−1 minute.

26. A method according to claim 1, wherein an instant $tf_{Cdi}$, at which the effects of the change in conductivity cease in an upstream conductivity curve, is calculated by estimating an area defined below the upstream conductivity curve, said instant $tf_{Cdi}$ being identified by the moment at which the area under the upstream conductivity curve takes on an average value below a predetermined threshold.

27. A method according to claim 1, wherein the conductivity values measured upstream from the filtration unit Cdi are filtered to eliminate long term fluctuations between such conductivity values.

28. A method according to claim 27, wherein only the inlet conductivity values Cdi measured within a significant time interval are filtered.

29. A method according to claim 27, wherein a mathematical filter is used to eliminate the long term fluctuations between the conductivity values measured upstream from the filtration unit Cdi, said filter being of the exponential type.

30. A method according to claim 29, wherein, after filtering, an upstream conductivity curve is determined by the following expression: $Cdi_{filt,i}$=(N−1)/N*$Cdi_{filt,i-1}$+1/N*Cdii−1, where N=filtering factor.

31. A method according to claim 30, wherein the filtering factor N is between 150 and 250 and a sampling frequency used to determine conductivity values Cdi ranges from 0.01 to 0.1 min.

32. A method according to claim 1, wherein the conductivity values measured downstream from the filtration unit Cdo are corrected on the basis of conductivity fluctuations generated in the conductivity values measured upstream from the filtration unit Cdi.

33. A method according to claim 1, wherein the conductivity values measured upstream from the filtration unit Cdi are filtered to eliminate long term fluctuations between the upstream conductivity values and wherein the conductivity values measured downstream from the filtration unit Cdo are corrected on the basis of the conductivity fluctuations generated in the conductivity values measured upstream from the filtration unit Cdi, the measured values of the downstream conductivity curve Cdo being corrected on the basis of the filtered conductivity values $Cdi_{filt}$ measured upstream.

34. A method according to claim 30, wherein the conductivity values measured downstream from the filtration unit Cdo are corrected on the basis of fluctuations generated in the conductivity values measured upstream from the filtration unit Cdi and wherein the corrected downstream conductivity curve is determined by the expression: $Cdo_{corr}$=Cdo+(Cdo2−$Cdo_{pre,mean}$)*$Cdi_{diff}$/step size, where $Cdi_{diff}$=$Cdi_{filt}$−$Cdi_{step,mean}$; step size=$Cdi_{pre,mean}$−$Cdi_{step,mean}$; Cdo2=conductivity value downstream from the filtration unit after the effects of the change in conductivity.

35. A method according to claim 14, wherein the conductivity values measured downstream from the filtration unit Cdo are corrected on the basis of the conductivity fluctuations generated in the conductivity values measured upstream from the filtration unit Cdi, wherein the corrected downstream conductivity curve fits the expression: $Cdo_{corr}=Cdo+(Cdo2-Cdo_{pre,mean})*Cdi_{diff}$/step size, where $Cdi_{diff}=Cdi_{filt}-Cdi_{step,mean}$; step size=$Cdi_{pre,mean}-Cdi_{step,mean}$, Cdo2=conductivity value downstream from the filtration unit after the effects of the change in conductivity; and wherein, for the purpose of calculating $Cdo_{corr}$, a preliminary estimate value of Cdo2 is used, said estimate being defined by the value that the function $Cdo\_1n_{clr}$ assumes at the instant $t=t0_{Cdo}$.

36. A method according to claim 1, further comprising the step of computing the downstream conductivity curve to determine a characteristic time tStartCF, beyond which the downstream conductivity curve has stabilized after undergoing the effects of the imposed change in conductivity.

37. A method according to claim 36, wherein said characteristic time tStartCF is given by the sum of two terms, a first term $t_{target}$, which is a function of the conductivity curve, and a second term tcbf, which is a function of the blood flow.

38. A method according to claim 37, wherein the second term tcbf is determined by the following relation: tcbf=16/60+260/Qb, where Qb=blood flow.

39. A method according to claim 6, further comprising the step of computing the downstream conductivity curve to determine a characteristic time tStartCF, beyond which the downstream conductivity curve has stabilized after undergoing the effects of the imposed change in conductivity, and said characteristic time tStartCF is given by the sum of two terms, a first term $t_{target}$, which is a function of the conductivity curve, and a second term tcbf, which is a function of the blood flow, the determination of the first term $t_{target}$ for calculating the characteristic time entailing the sub steps of: estimating an intermediate time $tA_{clr}$, deriving the first term $t_{target}$, said first term $t_{target}$ coinciding with the time that makes a straight line passing through points $(t0_{Cdo}; Cdo0)$ and $(tA_{clr}; CdoA)$ take on the value $Cdo_{pre,mean}$+step size, where Cdo0 and CdoA are the values taken on by curve Cdo at instants $t0_{Cdo}$ and $tA_{clr}$ where $Cdo_{pre,mean}$ is the average outlet conductivity prior to the effects of the change in conductivity.

40. A method according to claim 39, wherein the intermediate time $tA_{clr}$ is calculated using the function: unit_f=ln (sign*$(Cdi_{step,set}-Cdo)$/potential), and performing an interpolation with a least squares estimation on the data of the area between said function and the time axis of the x-coordinates in a predetermined interval of time, said intermediate time $tA_{clr}$ coinciding with the instant at which the interpolating function intersects the time axis, thereby taking on a value of zero.

41. A method according to claim 40, wherein the predetermined time interval for the least squares estimation of the function unit_f falls between a first instant of reversal in the blood line (tRev−1.5 min) and a second instant of reversal in the blood line tRev.

42. A method according to claim 1, further comprising the step of calculating conductivity at the outlet of the filtration unit after the imposed change in conductivity.

43. A method according to claim 42, wherein the step of calculating conductivity at the outlet of the filtration unit further comprises a sub step consisting in the least squares interpolation of a mathematical curve f, which is a function of $Cdi_{step,mean}$ and $Cdo_{corr}$, in a predetermined time interval.

44. A method according to claim 43, wherein the mathematical curve is determined by the following equation: f=ln (sign*$(Cdi_{step,mean}-Cdo_{corr})$).

45. A method according to claim 43, wherein said predetermined time interval falls between $tstartCF_{clr}$ and tstart $CF_{clr}$+1.5 min.

46. A method according to claim 43, wherein the step of calculating conductivity at the outlet of the filtration unit further comprises the sub step of creating an equation $Cdo\_1n_{clr}$, which is a function of $Cdi_{step,mean}$ and c(1) and c(2), where c(1) and c(2)=coefficients derived from the least squares interpolation of function f.

47. A method of calculating the filter clearance by means of a function relation of Cdo2, Cdo1, Cdi2 and Cdi1, said conductivities being calculated using the method according to claim 1.

48. A method according to claim 47, wherein the filter clearance is determined by the following equation:

$$K_e = (Q_d + Q_{UF}) \cdot \left(1 - \frac{Cdo2 - Cdo1}{Cdi2 - Cdi1}\right)$$

where $Cdi2=Cdi_{step,mean}$ or $Cdi_{set,step}$, $Cdi1=Cdi_{pre,mean}$ or $Cdi_{set,pre}$, $Cdo1=Cdo_{pre}(t=tCalc_{clr})$, Qd=flow of dialysate fluid, QUF=ultra filtration flow of dialysate fluids.

49. A method for calculating fistula flow, comprising the steps of: determining a filter clearance according to the method of claim 47; reversing blood flow inside the filtration unit, said reversal causing recirculation in the fistula and a consequent change in conductivity in the downstream conductivity curve; determining, by means of mathematical calculations, an outlet conductivity prior to the reversal of blood flow Cdon; determining a conductivity of the outlet process fluid Cdor following the reversal in blood flow; and, setting or estimating an inlet conductivity Cdi after the imposition of a change in conductivity.

50. A method according to claim 49, wherein the fistula flow is determined by the following formula:

$$Q_{aw} = (K_e - Q_{UF}) \cdot \left(\frac{Cdor - Cdi}{Cdon - Cdor}\right).$$

51. A method according to claim 50, wherein an actual fistula flow is obtained by correcting the value Qaw according to the following formula:

$$Q_a = \frac{Q_{aw}}{\left[\left(1 - \frac{Hct}{100}\right)*\left(1 - \frac{Tp}{1000}\right) + \frac{Hct}{100}*Fr\right]}$$

where Hct is the hematocrit, Tp is the total plasma protein content and Fr is the red cell water fraction=volume water in red cells/total volume of red cells.

52. A method according to claim 49, wherein the step of determining, by means of mathematical calculations, an outlet conductivity prior to the reversal in blood flow Cdon is achieved by creating a second function f as a function of $Cdi_{step,set}$ and Cdo.

53. A method according to claim 52, wherein the second function f is interpolated with a least squares estimation in a predetermined time interval.

54. A method according to claim 52, wherein the second function f is determined by the following equation: f=ln (sign*$(Cdi_{step,set}-Cdo)$).

55. A method according to claim 52, wherein the step of determining outlet conductivity prior to the reversal in blood flow Cdon further comprises the sub step of estimating the downstream conductivity curve of the filter as a function of $Cdi_{step,mean}$, and $c_{pre,acc}(1)$ and $c_{pre,acc}(2)$, where $c_{pre,acc}(1)$ and $c_{pre,acc}(2)$ are coefficients of the least squares interpolation performed on the second function f.

56. A method according to claim 55, wherein the sub step of estimation is made based on the relation: $Cdo-1n_{pre,acc}=Cdi_{step,mean}-sign*exp(c_{pre,acc}(1)*t+c_{pre,acc}(2))$.

57. A method according to claim 53, wherein said predetermined time interval falls between $t=tstartCF_{cri}$ and $t=t0_{acc}-[½]$ min.

58. A method according to claim 56, wherein the value Cdon is calculated by estimating the value of the function $Cdo-1n_{pre,acc}$ at the instant $t=tCalc_{acc}$.

59. A method according to claim 49, wherein the step of determining outlet conductivity after the reversal in blood flow Cdor is achieved by creating a second relation f as a function of $Cdi_{step,set}$ or $Cdi_{step,mean}$ and Cdo.

60. A method according to claim 59, wherein the second relation f is interpolated with a least squares estimation in a predetermined time interval.

61. A method according to claim 59, wherein the second relation f is determined by the following equation: $f=ln(sign*(Cdi_{step,set}-Cdo))$ or $f=ln(sign*(Cdi_{step,mean}-Cdo))$.

62. A method according to claim 59, wherein the step of determining, by means of mathematical calculations, the outlet conductivity after the reversal in blood flow Cdor further comprises the sub step of estimating a curve of the conductivity values at the filter outlet as a function of $Cdi_{step,mean}$, $c_{acc}(1)$, and $c_{acc}(2)$, where $c_{acc}(1)$ and $c_{acc}(2)$ are coefficients of the least squares interpolation performed on the second relation f.

63. A method according to claim 62, wherein the sub step of estimating the conductivity curve is performed by means of the relation: $Cdo1n_{acc}=Cdi_{step,mean}-sign*(exp(c_{acc}(1)*t+c_{acc}(2)))$.

64. A method according to claim 60, wherein said predetermined time interval falls between $t=tstartCF_{acc}$ and $t=tfcCdi-1$ minute.

65. A method according to claim 56, wherein the value Cdon is calculated by estimating the value of the function $Cdo\_ln_{pre,acc}$ at the instant $t=tCalc_{acc}$.

66. A method according to claim 65, wherein the reversal in blood flow is effected manually or automatically.

67. A method according to claim 66, wherein the calculation of $tCalc_{acc}$ comprises the following steps: filtering the current downstream conductivity curves; creating a mathematical relation f_flt, which is a function of $Cdi_{step,mean}$ and Cdo_flt; and, performing a least squares interpolation of said function in an established time interval.

68. A method according to claim 67, wherein the calculation of $tCalc_{acc}$ additionally comprises the steps of: creating a relation $Cdo\_ln_{acc,est}$, which is a function of $Cdi_{step,mean}$, $c_{acc,est}(1)$, and $c_{acc,est}(2)$, $c_{accest}(1)$ and $c_{acc,est}(2)$ being coefficients derived from the interpolation of the mathematical relation f_flt; and, constructing a further relation f<2> acc, which is the difference between $Cdo\_ln_{acc,est}$ and Cdo_flt.

69. A method according to claim 68, wherein the calculation of $tCalc_{acc}$ comprises the further sub steps of creating a difference function $diff\_f2_{acc}=f2_{acc}(i)-f2_{acc}(i-1)$ and standardizing said difference function, if necessary, to obtain the function: $f2_{der\_norm}=diff2_{acc}/min(diff-f2_{acc})$.

70. A method according to claim 69, wherein $t0_{acc,est}$ is the instant at which $f2_{der\_norm}$ first takes on a value greater than 0.5, $t0_{acc}$ preferably being defined as $t0_{acc}=t0_{acc,est}-0.1$ min.

71. A method according to claim 70, wherein in the case of a normal reversal in blood flow $t0_{acc}$ coincides with $tCalc_{acc}$.

72. A method according to claim 69, wherein tStartCF is given by the sum of the instant at which $f2_{der\_norm}$, after peaking, falls below the value of 0.2, plus an increment of 0.5 min.

73. A method of determining the conductivity of a process fluid downstream from a filtration unit in blood processing machines, said unit comprising a first compartment for the circulation of blood and a second compartment for the circulation of the process fluid, said method comprising the following steps:

creating a flow of fluid through the second compartment of a filtration unit;

imposing, for a predetermined time interval, a change in the conductivity of the process fluid at the inlet of the filtration unit in order to cause an induced conductivity change at the outlet;

measuring a predetermined number of conductivity values upstream and downstream from the filtration unit defining respectively upstream and downstream conductivity curves, determining, by means of a control unit making mathematical calculations, at least a characteristic time $t0_{Cdi}$ of the upstream conductivity curve;

determining, by means of a control unit making mathematical calculations, a corresponding preliminary estimate of a characteristic time $t0_{Cdo}$ of the downstream conductivity curve, the preliminary estimate of the characteristic time $t0_{Cdo}$ of the downstream conductivity curve corresponding to the instant at which the induced conductivity change downstream from the filtration unit occurs, said preliminary estimate comprising the following sub-steps:

a) determining the average conductivity at the outlet of the filtration unit $Cdo_{pre,mean}$ prior to the effects of the change in conductivity, said determination being made on the basis of an average of the measured conductivity values Cdo prior to the effects of the change;

b) comparing the measured conductivity values at the outlet of the filtration unit Cdo with the previously determined average outlet conductivity value $Cdo_{pre,mean}$;

c) estimating the instant at which the measured conductivity values Cdo appear constantly different than the previously calculated average outlet conductivity value $Cdo_{pre,mean}$;

correcting the preliminary estimate of the characteristic time $t0_{Cdo}$ value of the conductivity curve downstream from the filtration unit comprising:

a) creating a mathematical expression unit_f, which is a function of the conductivity values measured downstream from the filtration unit Cdo, and of the known change in the conductivity of the inlet fluid; the mathematical expression used being the following:

$$unit\_f=ln(sign*(Cdi_{step,set}-Cdo)/potential))$$

where $potential=Cdi_{step,mean}-Cdo_{pre,mean}$;
where $Cdi_{step,set}$=a value of the known change in conductivity at the filtration unit inlet;
where Cdo=conductivity values measured downstream from the filtration unit;
where $Cdi_{step,mean}$=inlet conductivity value after the change in conductivity;
where $Cdo_{pre,mean}$=average outlet conductivity value prior to the change in conductivity; and
performing a least squares estimation of said expression unit_f in a predetermined time interval;

b) performing a least squares interpolation on said mathematical expression unit_f in a predetermined time interval; the least squares estimation being performed on the mathematical expression unit_f and the estimate being called $$Cdo\_ln_{clr} = Cdi_{set,step} - \text{sign} * \exp(c_{clr}(1)*t + c_{clr}(2))$$

where $c_{clr}(1)$ and $c_{clr}(2)$ are coefficients derived from the least squares interpolation of the mathematical expression unit_f;

c) creating a mathematical function f_norm, which is a function of coefficients $c_{clr}(1)$ and $c_{clr}(2)$ derived from the previous least squares interpolation, a function of the known change in conductivity $Cdi_{step,set}$ of the inlet fluid and a function of the conductivity values downstream from the filtration unit Cdo, the mathematical function used being the following:

$$f\_norm = (f2_{clr} - \min*(f2_{clr}))/\max(f2_{clr} - \min(f2_{clr}))$$

where $f2_{clr} = Cdo\_ln_{clr} - Cdo$ d) performing a least squares interpolation on the mathematical function f_norm within a predetermined interval of values, e) creating a mathematical estimation function f_norm_est, which is a function of the coefficients $c_{clr}(3)$ and $c_{clr}(4)$ derived from the least squares interpolation of the mathematical function, the mathematical estimation function used being the following:

$$f\_norm\_est = \exp(c_{clr}(3)*t + c_{clr}(4))$$

where $c_{clr}(3)$ and $c_{clr}(4)$ are the coefficients derived from the least squares interpolation of the natural logarithm of the mathematical function f_norm; the corrected value $t0_{Cdo}$ of the characteristic time of the conductivity curve downstream from the filtration unit coinciding with the instant at which the mathematical estimation function f_norm_est takes on a value of one;

synchronizing the upstream and downstream conductivity curves on the basis of the characteristic times $t0_{Cdi}$ and $t0_{Cdo}$ determined by the upstream and downstream curves to enable a comparison of the respective conductivity values; and comparing the upstream conductivity curve and the downstream conductivity curve after the respective conductivity curves have been synchronized to determine one or more downstream conductivity values;

wherein the measured values of the downstream conductivity curve Cdo are corrected on the basis of conductivity fluctuations generated in the measured values of the upstream conductivity curve Cdi by computing the deviation that the upstream conductivity curve Cdi does from its mean value over the change in the conductivity, and then adjusting the downstream conductivity curve Cdo in proportion to said deviation.

74. A blood treatment machine comprising:
at least a filtration unit with a first compartment for the circulation of blood and a second compartment for the circulation of the treatment fluid, said first and second compartments being separated by interposing at least a semi-permeable membrane;
means for changing the conductivity of the treatment fluid upstream from the filtration unit;
at least a first sensor installed upstream from the filtration unit and a second sensor installed downstream from the filtration unit, wherein said first sensor measures the conductivity of a process fluid upstream from the filtration unit and said second sensor measures the conductivity of the process fluid downstream from the filtration unit; and
a control unit governing said devices in order to change the conductivity of the process fluid, said control unit being configured to receive conductivity signals from the first and second sensors, the control unit being configured to execute the steps of claim 1 for calculating the conductivity of the fluid downstream from the filtration unit.

75. A method according to claim 15, wherein the predetermined interval of values for performing the least squares interpolation on the mathematical function f_norm is between 0.2 and 0.8.

76. A method according to claim 27, wherein the significant time interval corresponds to the interval falling between an instant at which the change in conductivity occurs in the upstream conductivity curve, $t0_{Cdi}+0.5$ minutes, and an instant at which the effects of the change in conductivity cease in the same curve, $tf_{clr}-0.5$ minutes.

77. A method according to claim 30, wherein the filtering factor N is 200 and a sampling frequency used to determine conductivity values Cdi is 0.033 min.

78. A method for determining conductivity of a treatment fluid downstream from a filtration unit in blood processing machines, said unit comprising a first compartment for the circulation of blood and a second compartment for the circulation of the treatment fluid, separated from the first compartment by interposing at least a semi-permeable membrane; said method comprising the steps of:
creating a flow of treatment fluid through the second compartment of the filtration unit;
imposing, for a predetermined time interval, a change in the conductivity of the treatment fluid at the inlet of the filtration unit in order thereby to cause an induced conductivity change in the fluid at the outlet of said filtration unit;
measuring a predetermined number of conductivity values Cdo downstream from the filtration unit and belonging to a conductivity curve downstream from the filtration unit, wherein the method further comprises the steps of:
defining at least one interpolating mathematical function for the purpose of estimating the pattern of the conductivity curve Cdo downstream from the filtration unit in an interval of time after the occurrence of the induced conductivity change; wherein the mathematical function has the form:

$$Cdo\_ln_{clr} = Cdi_{step,mean} - \text{sign}*\exp(c(1)*t + c(2))$$

where c(1) c(2) are coefficients derived from the least squares interpolation of the mathematical function and $Cdi_{step,mean}$=inlet conductivity value after the change in conductivity;
determining a characteristic measuring time $tcalc_{clr}$;
calculating by means of a control unit the value of the interpolating mathematical function at said characteristic measuring time $tcalc_{clr}$, said value representing the conductivity value Cdo2 of the process fluid downstream from the filtration unit after the induced conductivity change, wherein the determination of the characteristic measuring time $tcalc_{clr}$ comprises the following sub steps:
estimation of an intermediate time $tA_{clr}$ representative of a transient due to the induced conductivity change in the fluid, said time $tA_{clr}$ depending on at least a filtration unit volume, blood and treatment fluid flows and the change in the conductivity of the treatment fluid at the inlet of the filtration unit; wherein the intermediate time $tA_{clr}$ is calculated using the function:

$$\text{unit}\_f = \ln(\text{sign}*(Cdi_{step,set} - Cdo)/\text{potential})$$

where potential=$Cdi_{step,mean} - Cdo_{pre,mean}$;

where $Cdi_{step,set}$=a value of the known change in conductivity at the filtration unit inlet;

where Cdo=conductivity values measured downstream from the filtration unit;

where $Cdi_{step,mean}$=inlet conductivity value after the change in conductivity;

where $Cdo_{pre,mean}$=average outlet conductivity value prior to the change in conductivity;

and by performing an interpolation with least squares estimation on the data of an area falling between said function and the x-coordinate time axis in a predetermined time interval, said intermediate time $tA_{clr}$ coinciding with the instant at which the interpolating function intersects the time axis, the area taking on a value of zero; and correction of the intermediate time $tA_{clr}$ through the addition of a second time term tcbf, which is a function of blood flow, $tcalc_{clr}$ being defined as $tcalc_{clr}=tA_{clr}+tcbf$, Cdo2 value being the value of the equation at $t=tcalc_{clr}$.

* * * * *

UNITED STATES PATENT AND TRADEMARK OFFICE
CERTIFICATE OF CORRECTION

PATENT NO. : 7,815,809 B2
APPLICATION NO. : 11/299840
DATED : October 19, 2010
INVENTOR(S) : Olof Jansson et al.

Page 1 of 1

It is certified that error appears in the above-identified patent and that said Letters Patent is hereby corrected as shown below:

In claim 16, column 15, line 23, after "of" delete --Cdi--.

In claim 73, column 21, line 18 & 19, delete asterisk after "min".

In claim 76, column 22, line 19, "$tf_{clr}$-0.5 minutes" should read --$tf_{cdi}$-0.5 minutes--.

Signed and Sealed this
Twenty-fifth Day of January, 2011

David J. Kappos
*Director of the United States Patent and Trademark Office*